US00PP25812P2

(12) United States Plant Patent
Zaiger et al.

(10) Patent No.: US PP25,812 P2
(45) Date of Patent: Aug. 18, 2015

(54) PEACH TREE NAMED 'RICH SNOW'

(50) Latin Name: *Prunus persica*
Varietal Denomination: RICH SNOW

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 65 days.

(21) Appl. No.: 13/999,218

(22) Filed: Jan. 31, 2014

(51) Int. Cl.
*A01H 5/08* (2006.01)

(52) U.S. Cl.
USPC ..... Plt./195

(58) Field of Classification Search
USPC ..... Plt./195
CPC ..... A01H 5/0868; A01H 5/0837; A01H 5/08
See application file for complete search history.

*Primary Examiner* — Kent L Bell

(57) ABSTRACT

A new and distinct variety of peach tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. The tree being a regular and productive bearer of medium to large size, white flesh fruit.
2. The tree with vigorous, upright growth.
3. Producing fruit with an attractive red skin color.
4. Fruit with good flavor and very good eating quality.
5. Fruit with good storage and shipping quality.

1 Drawing Sheet

Botanical designation: *Prunus persica.*
Variety denomination: 'RICH SNOW'.

BACKGROUND OF THE VARIETY

1. Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of peach tree was originated and asexually reproduced by us in our experimental orchard located near Modesto, Stanislaus County, Calif.

2. Prior Varieties

Among the existing varieties of peach trees, which are known to us, and mentioned herein, 'Snow Lady' Peach (U.S. Plant Pat. No. 25,093) and 'Snow Angel' Peach (U.S. Plant Pat. No. 18,750).

STATEMENT REGARDING FEDERALLY SPONSORED RESEARCH AND DEVELOPMENT

Not applicable.

ORIGIN OF THE VARIETY

The new and distinct variety of peach tree (*Prunus persica*) was developed by us in our experimental orchard located near Modesto, Calif. from open pollinated seed of 'Snow Lady' Peach (U.S. Plant Pat. No. 25,093). A large number of these open pollinated peach seedlings were grown and budded to older trees of 'Nemaguard' Rootstock (non-patented) to accelerate rapid fruit production. Under close and careful observation we recognized the desirable tree and fruit characteristics of the present variety and selected it in 2009 for additional asexual propagation and commercialization.

ASEXUAL REPRODUCTION OF THE VARIETY

Asexual reproduction of the new and distinct variety of peach tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new variety of peach tree (*Prunus perisca*) is of large size, vigorous, upright growth and a productive and regular bearer of medium to large size, clingstone fruit with a mild, sweet, sub-acid flavor and very good eating quality. The fruit is further characterized by having an attractive red skin color, firm, white flesh and being relatively uniform in size throughout the tree. In comparison to its seed parent 'Snow Lady' Peach (U.S. Plant Pat. No. 25,093) the fruit of the new variety is 6 days later in maturity and has a higher Brix 14.5° compared to 12.0°. In comparison to the commercial variety 'Snow Angel' Peach (U.S. Plant Pat. No. 18,750) the fruit of the new variety is approximately 16 days later in maturity.

DESCRIPTION OF THE PHOTOGRAPH

The accompanying color photographic illustration shows typical specimens of the foliage and fruit of the present new peach variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 5 year old tree and the colors are as nearly true as is reasonably possible in a color representation of this type.

DESCRIPTION OF THE VARIETY

The following is a detailed botanical description of the new variety of peach tree, its flowers, foliage and fruit, as based on observations of 5 year old specimens grown near Modesto, Calif., with color in accordance with Munsell Book of Color published in 1958.

Tree:

*Size*.—Large, usually pruned to 3 to 3.5 meters in height and width for economical harvesting of fruit. Size varies with different cultural practices.

*Vigor*.—Vigorous, growth of 1.5 to 2 meters in height the first growing season. Varies with soil type, fertility of soil and climatic conditions.

*Form*.—Upright, usually pruned to vase shape.

*Branching habit*.—Upright, crotch angle approximately 35°, increases with heavy crop load.

*Productivity*.—Productive, thinning and spacing of fruit necessary for desired market size fruit. Number of fruit varies with climatic conditions during bloom time.

*Bearer*.—Regular, has had adequate fruit set 3 consecutive years. No alternate bearing observed.

*Fertility*.—Self fertile.

*Density*.—Medium dense, usually pruned to vase shape to allow sunlight to center of tree to enhance fruit color and health of fruit wood.

*Hardiness*.—Hardy in all stone fruit growing areas of California. Tree grown in USDA Hardiness Zone 9. Winter chilling requirement approximately 400 hours at or below 45° F.

Trunk:

*Size*.—Large. Average circumference of 61.0 cm at 25.7 cm above ground on a 5 year old tree.

*Stocky*.—Medium stocky.

*Texture*.—Medium shaggy, roughness increases with age.

*Color*.—Varies from 2.5Y 4/2 to 5Y 4/2.

Branches:

*Size*.—Medium. Average circumference 14.9 cm at 1.2 meters above ground. Crotch angle approximately 35°, increases with heavy crop load.

*Surface texture*.—New growth relatively smooth. Mature growth medium rough, roughness increases with age.

*Lenticels*.—Average number 34 in a 25.8 sq cm section. Average length 3.0 mm. Average width 1.7 mm. Color varies from 10YR 4/6 to 10YR 4/8.

*Color*.—New growth varies from 5GY 6/6 to 5R 3/6. Old growth varies from 7.5YR 2/4 to 10YR 3/4, varies with age of growth.

Leaves:

*Size*.—Medium to large. Average length 127.4 mm. Average width 38.1 mm.

*Form*.—Lanceolate.

*Apex*.—Acuminate.

*Base*.—Cuneate.

*Margin*.—Serrulate.

*Thickness*.—Medium.

*Surface texture*.—Upper surface relatively smooth, slight indentations over midrib and leaf veins. Lower surface relatively smooth, except for small ridges created by midrib and pinnate venation. Both upper and lower surfaces glabrous.

*Petiole*.—Average length 7.2 mm. Average width 1.6 mm. Longitudinally grooved. Surface glabrous. Color varies from 5GY 5/6 to 5GY 4/6.

*Glands*.—Type — reniform. Size — medium to large. Average length 1.3 mm. Average diameter 0.9 mm. Number varies from 3 to 5, average number 4. Located primarily on base of leaf blade and upper portion of petiole. Color varies from 5GY 5/4 to 5GY 5/6.

*Stipules*.—Average number 2. Average length 7.7 mm. Edges — pectinate. Color varies from 5GY 6/6 to 5GY 5/8.

*Color*.—Upper surface varies from 7.5GY 3/4 to 7.5GY 3/6. Lower surface varies from 5GY 4/4 to 7.5GY 4/4. Midvein color varies from 5GY 8/6 to 5GY 7/6.

Flower buds:

*Size*.—Medium to large. Average length 19.6 mm. Average diameter 9.4 mm.

*Hardiness*.—Hardy with respect to California winters.

*Form*.—Conical, becoming elongated just before opening.

*Pedicel*.—Average length 3.7 mm. Average width 1.3 mm. Color varies from 2.5GY 6/6 to 5GY 7/6.

*Color*.—Varies from 5RP 7/8 to 5RP 7/10.

Flowers:

*Blooming period*.—Date of First Bloom Feb. 17, 2013. Date of Petal Fall Feb. 27, 2013, varies slightly with climatic conditions.

*Size*.—Medium to large. Average height 20.1 mm. Average diameter 33.1 mm.

*Petals*.—Normally 5, alternately arranged to sepals. Size — large. Average length 18.7 mm. Average width 18.0 mm. Form — obovate. Arrangement — overlapping. Margin — sinuate. Color varies from 5RP 8/4 to 5RP 8/6. Both upper and lower surfaces glabrous.

*Sepals*.—Normally 5, alternately arranged to petals. Size — medium. Average length 5.8 mm. Average width 5.4 mm. Shape — ovate. Margin — entire. Color — upper surface varies from 5GY 5/6 to 5R 3/6. Lower surface varies from 5R 2/2 to 7.5R 3/2. Surface — upper surface glabrous, lower surface pubescent.

*Stamens*.—Average number per flower 42. Average filament length 15.3 mm. Filament color varies from N 9.5/(white) to 5RP 6/8. Anther color varies from 7.5R 3/10 to 5Y 8/8.

*Pollen*.—Self fertile. Color varies from 2.5Y 7/10 to 5Y 7/10.

*Pistil*.—Normally one. Surface pubescent. Average length 16.9 mm. Position of stigma an average of 1.4 mm below anthers. Color varies from 7.5Y 8/6 to 10Y 8/6.

*Fragrance*.—Moderate.

*Color*.—Varies from 7.5RP 8/4 to 7.5RP 7/4.

*Number flowers per flower bud*.—Normally one.

*Pedicel*.—Average length 3.7 mm. Average width 1.3 mm. Color varies from 10Y 7/6 to 2.5GY 6/6.

Fruit:

*Maturity when described*.—Firm ripe.

*Date of first picking*.—May 25, 2013.

*Date of last picking*.—Jun. 7, 2013, varies slightly with climatic conditions.

*Size*.—Medium to large. Average length 58.1 mm. Average transversely in suture plane 69.8 mm. Average weight 176.1 grams, varies slightly with fertility of the soil, amount of thinning and climatic conditions.

*Form*.—Globose.

*Suture*.—Nearly smooth, extends from base to apex.

*Ventral surface*.—Nearly smooth.

*Apex*.—Slightly retuse.

*Base*.—Retuse.

*Stem cavity*.—Rounded to slightly elongated in suture plane. Average depth 3.8 mm. Average diameter 8.4 mm.

Stem:

*Size*.—Small to medium. Average length 8.1 mm. Average diameter 3.5 mm.

*Color*.—Varies from 5GY 6/8 to 5GY 5/8.

Flesh:

*Ripens*.—Evenly.

*Texture*.—Firm, meaty.

*Fibers*.—Few, small, tender.

*Firmness*.—Good, comparable to other commercial varieties.

*Aroma*.—Moderate.

*Amydgalin*.—Undetected.

*Eating quality*.—Very good.

*Flavor*.—Good, mild, sweet, sub-acid.

*Juice*.—Moderate amount, enhances flavor.

*Brix*.—Average Brix 14.5°, varies slightly with climatic conditions.

*Color*.—Varies from 5Y 8.5/4 to 7.5Y 9/2.

*Pit cavity*.—Average length 31.0 mm. Average width 27.0 mm. Average depth 11.2 mm. Color 7.5Y 9/2.

Skin:

*Thickness*.—Medium.

*Surface*.—Smooth to very slightly waffled.

*Pubescence*.—Moderate amount, short in length.

*Tendency to crack*.—None.

*Color*.—Ground color varies from 10Y 9/2 to 2.5GY 9/2, overspread with 5R 3/4 to 5R 5/6.

*Tenacity*.—Tenacious to flesh.

*Astringency*.—Undetected.

Stone:

*Type*.—Clingstone.

*Size*.—Large. Average length 29.7 mm. Average width 20.3 mm. Average thickness 25.5 mm.

*Form*.—Ovoid.

*Base*.—Flat.

*Apex*.—Slightly pointed. Average length 1.2 mm.

*Surface*.—Pitted throughout, pits vary from round to elongated.

*Sides*.—Unequal, one side extending further from the suture plane.

*Ridges*.—Relatively smooth, extending from the base toward apex.

*Tendency to split*.—None.

*Color*.—Varies from 10YR 6/6 to 10YR 6/8 when dry.

Kernel:

*Size*.—Medium. Average length 15.3 mm. Average width 10.1 mm. Average depth 6.9 mm.

*Form*.—Ovoid.

*Viability*.—Partially viable, incomplete embryo development in some fruit.

*Skin color*.—Varies from 7.5Y 9/2 to 7.5Y 9/4.

Use: Dessert.

*Market*.—Local and long distance.

Keeping quality: Good, held firm in cold storage at 38° to 42° F. for 3 weeks without internal breakdown of flesh or appreciable loss of flavor.

Shipping quality: Good, minimal skin scarring or flesh bruising during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of peach tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of peach tree (*Prunus persica*), substantially as illustrated and described.

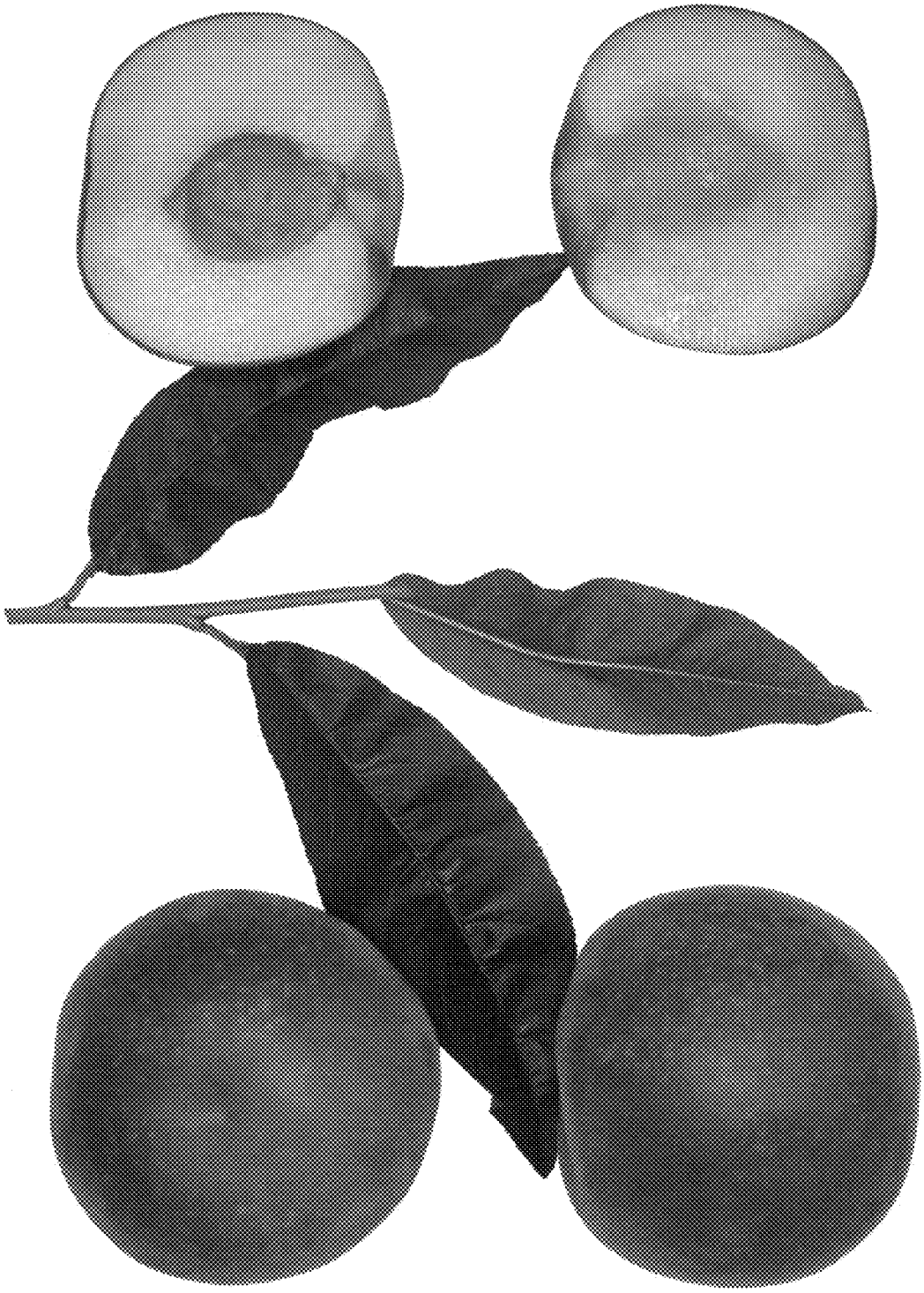

* * * * *